United States Patent [19]

McFadden

[11] 4,055,987
[45] Nov. 1, 1977

[54] LIQUID CHROMATOGRAPH/MASS SPECTROMETER INTERFACE

[75] Inventor: William H. McFadden, San Jose, Calif.

[73] Assignee: Finnigan Corporation, Sunnyvale, Calif.

[21] Appl. No.: 664,058

[22] Filed: Mar. 4, 1976

[51] Int. Cl.² .................................................. G01N 31/08
[52] U.S. Cl. .............................. 73/61.1 C; 23/254 EF; 210/198 C
[58] Field of Search ................. 73/61.1 C, 23.1, 61.3; 23/254 EF; 210/198 C, 24 C

[56] References Cited

U.S. PATENT DOCUMENTS

| | | |
|---|---|---|
| 3,128,619 | 4/1964 | Lieberman .............................. 73/23.1 |
| 3,533,751 | 10/1970 | Maggs .............................. 73/61.3 UX |
| 3,566,677 | 3/1971 | Cole et al. .............................. 73/61.3 |
| 3,744,973 | 7/1973 | Dubsky .............................. 23/254 EF |
| 3,788,479 | 1/1974 | Szakasits .............................. 210/198 C |
| 3,929,004 | 12/1975 | Gunew et al. .............................. 73/61.1 C |

FOREIGN PATENT DOCUMENTS

| | | |
|---|---|---|
| 5,679 | 1/1972 | Japan .............................. 210/198 C |
| 277,384 | 10/1970 | U.S.S.R. .............................. 23/254 EF |

Primary Examiner—Richard C. Queisser
Assistant Examiner—Joseph W. Roskos
Attorney, Agent, or Firm—Flehr, Hohbach, Test, Albritton & Herbert

[57] ABSTRACT

A liquid chromatograph/mass spectrometer interface for permitting the efficient and continuous introduction of an effluent solution from liquid chromatograph into a quadrupole mass spectrometer or any other vacuum analytical system includes a thin ribbon in the form of a loop which at one end receives liquid chromatograph effluent which is passed through one or more vacuum locks to remove residual solvent. At the other end the film of solute or low volatility sample is flash vaporized into the ionization chamber of the mass spectrometer. The interface device is also used to sample dilute solutions from any other source and can be used in a continuous mode, in a single sample mode, or for automatic but intermittent sample introduction.

6 Claims, 2 Drawing Figures

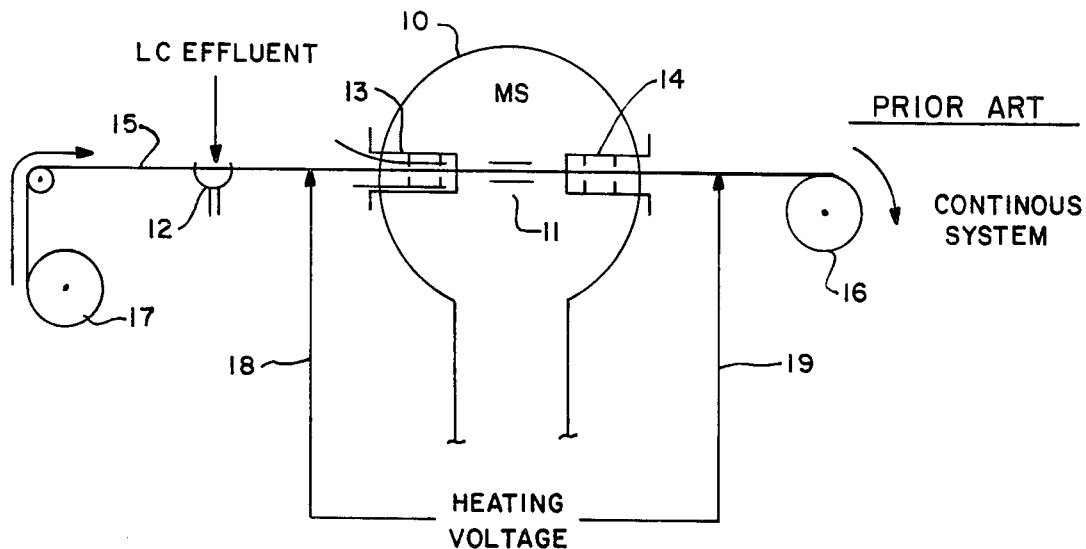
FIG.—1
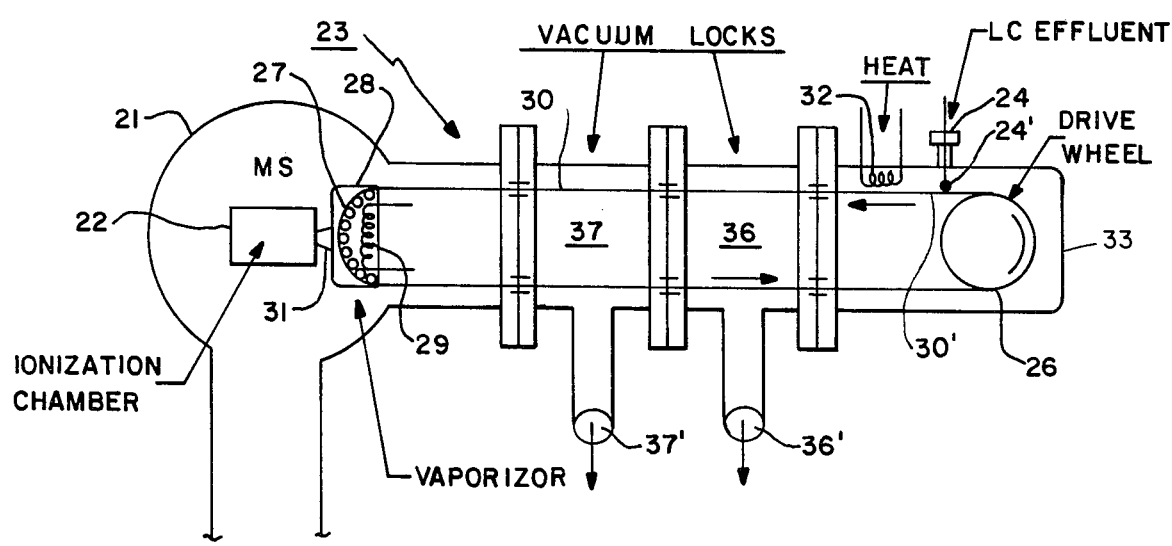
FIG.—2

LIQUID CHROMATOGRAPH/MASS SPECTROMETER INTERFACE

BACKGROUND OF THE INVENTION

The present invention is directed to methods of efficient sampling of dilute solutions into a mass spectrometer and more specifically to provide an interface that permits continuous introduction of a sample effluent from a liquid chromatograph into the ionization chamber of a mass spectrometer. Moreover, the mass spectrometer may be of any known type.

FIG. 1 illustrates a prior art liquid chromatograph mass spectrometer (lc/ms) interface which includes a mass spectrometer 10 with an ionizing region 11 the remainder of the mass spectrometer being typical of the quadrupole mass filter type. The liquid chromatograph effluent is placed into a cup 12 through which a moving wire 15 moves to pick up the fluid to pass it into the mass spectrometer through a first two stage vacuum lock 13 and the wire passes out through a second vacuum lock 14 it is taken up by take-up reel 16. The supply reel is located at 17. A heating voltage is applied across the points 18 and 19, to cause that portion of the moving wire 15 to vaporize the effluent carried by it. With this type of system approximately only 1% of the effluent reaches the ionization region. In addition, there is no specific heating technique for the removal of the solvent from the effluent. Further, said device cannot be used with a conventional magnetic mass spectrometer. The presence of the wire in the ion source also distorts the electric field in the quadrupole source and thereby impairs performance.

OBJECTS AND SUMMARY OF THE INVENTION

It is, therefore, an object of the present invention to provide an improved lc/ms interface which permits efficient and continuous introduction of the effluent solute from a liquid chromatograph to a mass spectrometer.

It is another object of the invention to provide an interface as above which excludes most of the volatile liquid chromatography solvent.

It is further intended that said interface will be used as a continuous sampling device to provide efficient introduction into the mass spectrometer of any dilute solution containing a low volatility solute in a high volatility solvent. The interface can function on a single batch sample or with a programmed individual sample injection system.

In accordance with the above objectives there is provided an interface for permitting efficient continuous introduction of any dilute solution into the ionization chamber of a mass spectrometer. A thin ribbon in the form of a loop is provided along with driving means for continuous moving of the ribbon. Means receive the solution and deposit it on the moving ribbon. A vaporization chamber is in close proximity to the ionization chamber of the mass spectrometer including a turn around for the loop. Heating means vaporize the deposited solution for introduction into the ionization chamber.

BRIEF DESCRIPTION OF THE DRAWINGS

FIG. 1 is a diagrammatic view of a liquid chromatograph/mass spectrometer interface illustrating the prior art; and FIG. 2 is a diagrammatic view of an improved liquid chromatograph/mass spectrometer interface embodying the present invention.

BRIEF DESCRIPTION OF THE PREFERRED EMBODIMENT

Referring now to FIG. 2, a typical mass spectrometer 21 with a standard ionization chamber 22 is illustrated. An interface generally indicated by 23 couples the ionization chamber to a source of dilute solution such as a liquid chromatograph effluent indicated at 24. A thin ribbon 30 of inert metallic material generally though not restricted to metal such as stainless steel is in the form of a loop. Near the liquid chromatograph effluent entrance 24 the ribbon is mounted on a drive wheel 26; the other end of the loop is turned around on a set of ten tungsten pins 27 which are in the form of an arc and are located in a flash vaporization chamber 28 contiguous to the ionization chamber 22.

The vaporization chamber 28 includes a heating coil 29 which is set in quartz to provide, in addition to thermal heating, infrared heating or radiation type heating. The vaporization chamber thus provides for flash vaporization of the effluent placed upon ribbon 30 as it passes through said chamber. Chamber 28 is connected to ionization chamber 22 by a nose cone type construction 31 where the narrow end of the cone enters into the ionization chamber 22.

The effluent entrance 24 which is also the output of the chromatograph is in the form of a small bore diameter pipe of, for example, 0.005 inches inner diameter and contacts at the area 30' of the ribbon which is flexible to thus lay down a smooth film of effluent. In other words, the end 24' of the pipe 24 is in flexible contact with the ribbon.

A heat source 32 located adjacent the effluent input point 30' heats the effluent to apply preliminary evaporation. Depending on the type of solvent used, this may or may not be necessary. For example, for a relatively volatile light solvent such as pentane it is not necessary while being necessary for heptane. The drive wheel and the heater 32 and the nozzle input 24 along with the ribbon are all in a closed portion 33 which is at substantially atmospheric pressure but may be filled with an inert gas such as helium or nitrogen. Next, along the line of the ribbon 30 a pair of vacuum locks 36 and 37 are provided with respective pump outlets 36' and 37' where the residual solvent is removed from the effluent on the ribbon 30 while at the same time excess air is excluded. Finally, the flash vaporizor 28 provides a rapid volatilization of the solute into the mass spectrometer ion chamber through the cone shaped connection 31.

The efficient removal of the solvent in the vacuum locks 36 and 37 premits operation of the mass spectrometer in the electron impact mode, chemical ionization mode, atmospheric ionization mode or any other selected ionization process. With the foregoing technique, more than 99.999% of the volatile liquid chromatography solvent is excluded. Moreover, the transfer line which includes the thin metallic ribbon 30 can hold up to 2 cubic centimeters per minute of the liquid chromatography effluent during the first evaporation stage. Thus, this provides for efficient transfer of the solute into the ionization chamber.

What is claimed is:

1. An interface for permitting efficient continuous introduction of any dilute solution into the ionization chamber, having an entrance port, of a mass spectrometer comprising: a thin ribbon in the form of a loop; driving means for continuous moving of said ribbon; means for receiving said solution and depositing it on said moving ribbon; a vaporization chamber including a turn-around for said loop in close proximity to said entrance port of said ionization chamber of said mass spectrometer and heating means for vaporizing said deposited solution for introduction into said ionization chamber.

2. An interface as in claim 1 including at least one intermediate vacuum lock for pumping out solvent from said solution.

3. An interface as in claim 1 wherein said heating means is in close proximity to said turn-around.

4. An interface as in claim 1 where said dilute solution is the effluent from a liquid chromatograph.

5. An interface as in claim 1 where said turn-around includes a plurality of pins arranged in the form of an arc around which said loop is turned the center of curvature of said arc being in close proximity to said port.

6. An interface for permitting efficient continuous introduction of any dilute solution into the ionization chamber, having an entrance port, of a mass spectrometer comprising: a thin ribbon in the form of a loop; driving means for continuous moving of said ribbon; means for receiving said solution and depositing it on said moving ribbon; a vaporization chamber including a turn-around for said loop in close proximity to said entrance port of said ionization chamber of said mass spectrometer and heating means for vaporizing said deposited solution for introduction into said ionization chamber; first and second series connected vacuum locks connected directly to said mass spectrometer through which said loop is moved after said solution is deposited; and means for pumping out solvent from each of said locks.

* * * * *